United States Patent
Atiyeh

(10) Patent No.: US 11,180,779 B2
(45) Date of Patent: Nov. 23, 2021

(54) SYSTEM AND METHOD OF BIOCATALYTIC CONVERSION FOR PRODUCTION OF ALCOHOLS, KETONES, AND ORGANIC ACIDS

(71) Applicant: The Board of Regents for Oklahoma State University, Stillwater, OK (US)

(72) Inventor: Hasan K. Atiyeh, Stillwater, OK (US)

(73) Assignee: The Board of Regents for Oklahoma State University, Stillwater, OK (US)

(*) Notice: Subject to any disclaimer, the term of this patent is extended or adjusted under 35 U.S.C. 154(b) by 0 days.

(21) Appl. No.: 16/604,242

(22) PCT Filed: Apr. 12, 2018

(86) PCT No.: PCT/US2018/027285
§ 371 (c)(1),
(2) Date: Oct. 10, 2019

(87) PCT Pub. No.: WO2018/191487
PCT Pub. Date: Oct. 18, 2018

(65) Prior Publication Data
US 2020/0157580 A1    May 21, 2020

Related U.S. Application Data

(60) Provisional application No. 62/484,525, filed on Apr. 12, 2017.

(51) Int. Cl.
| | |
|---|---|
| *C12P 7/06* | (2006.01) |
| *C12M 1/00* | (2006.01) |
| *C12N 1/20* | (2006.01) |
| *C12N 1/22* | (2006.01) |
| *C12P 7/16* | (2006.01) |
| *C12P 7/28* | (2006.01) |
| *C12P 7/52* | (2006.01) |
| *C12P 7/54* | (2006.01) |

(52) U.S. Cl.
CPC ............ *C12P 7/065* (2013.01); *C12M 21/12* (2013.01); *C12M 23/58* (2013.01); *C12N 1/20* (2013.01); *C12N 1/22* (2013.01); *C12P 7/16* (2013.01); *C12P 7/28* (2013.01); *C12P 7/52* (2013.01); *C12P 7/54* (2013.01)

(58) Field of Classification Search
CPC ................................. C12P 7/06; C12P 7/16
See application file for complete search history.

(56) References Cited

U.S. PATENT DOCUMENTS

| | | | |
|---|---|---|---|
| 8,293,509 B2 | 10/2012 | Simpson et al. | |
| 2010/0105115 A1 | 4/2010 | Simpson et al. | |
| 2010/0304437 A1 | 12/2010 | Garner et al. | |
| 2010/0323417 A1 | 12/2010 | Simpson et al. | |
| 2011/0306101 A1 | 12/2011 | De Crecy | |
| 2016/0068919 A1* | 3/2016 | Chen ....................... C12R 1/145 | 435/141 |
| 2019/0218505 A1* | 7/2019 | Papoutsakis ............. C12N 1/20 | |

FOREIGN PATENT DOCUMENTS

WO       2006042551 A1      4/2006

OTHER PUBLICATIONS

E.I. Khamaisehj et al. "Enhanced Butanol Production by Clostridium acetobutylicum NCIMB 13357 Grown on Date Fruit as Carbon Source in P2 Medium", The Scientific World Journal, Article ID 395754, pp. 1-7 (Year: 2014).*
K. Liu et al. "Process development for biological production of butanol from Eastern redcedar", Bioresource Technology 176: 88-97. (Year: 2015).*
Youn, Guk Hee; "Bioethanol and Biobutanol Production with Clostridium Carboxidivorans, Clostridium Beijerinckii, and Co-Culture from Biomass: Carbon Dioxide/Hydrogen Gas vs. Glucose Fermentation," Thesis for BS in Chemical Engineering, The Ohio State University, Sep. 12, 2017; 141 pages.
Hassan, et al.; "In Situ Hydrogen, Acetone, Butanol, Ethanol and Microdiesel Production by Clostridium acetobutylicum ATCC 824 from Oleaginous Fungal Biomass," Anaerobe (2015), 34:125-131.
Maddipati, P. "Ethanol Production from Syngas by Clostridium Strain P11 Using Corn Steep Liquor as a Nutrient Replacement," Degree of Master of Science Thesis. Graduate College of the Oklahoma State University (May 2010),83 pages.
Upkong, M.; "Enhancing Alcohol Production in Clostridium Carboxidivorans Strain P7(T) and the Role of Tandem ADH Genes," A Dissertation Submitted to the Graduate Faculty for the Degree of Doctor of Philosophy. Graduate College—University of Oklahoma (2014); p. XIV, p. 121, second paragraph.
International Search Report, dated Jun. 29, 2018, in PCT/US18/27285, filed Apr. 12, 2018.
Written Opinion of the International Searching Authority, dated Jun. 29, 2018, in PCT/US18/27285, filed Apr. 12, 2018.
U.S. Appl. No. 16/800,541; filed Feb. 25, 2020; Office Action dated Sep. 10, 2021.

* cited by examiner

*Primary Examiner* — Tekchand Saidha
(74) *Attorney, Agent, or Firm* — Dunlap Codding, P.C.

(57) ABSTRACT

Biocatalytic conversion systems and methods of producing and using same that have improved yields are disclosed. The systems and methods involve co-fermentation of sugars and gaseous substrates for alcohol, ketone, and/or organic acid production. The systems and methods may include biocatalytically converting at least one sugar substrate into at least one of alcohol, at least one ketone, and/or at least one organic acid. The systems and methods may further include biocatalytically converting gases that comprise $CO_2$ and $H_2$ to at least one alcohol and/or at least one organic acid, thereby adding extra revenue to biorefineries.

22 Claims, 5 Drawing Sheets

SYSTEM AND METHOD OF BIOCATALYTIC CONVERSION FOR PRODUCTION OF ALCOHOLS, KETONES, AND ORGANIC ACIDS

CROSS REFERENCE TO RELATED APPLICATIONS

This application is a US National Stage Application under 35 USC § 371 of International Application No. PCT/US2018/27285, filed Apr. 12, 2018; which claims benefit under 35 U.S.C. 119(e) of U.S. Provisional Application Ser. No. 62/484,525, filed Apr. 12, 2017, the entirety of which is hereby expressly incorporated herein by reference.

STATEMENT REGARDING FEDERAL SPONSORED RESEARCH OR DEVELOPMENT

This invention was made with U.S. Government support under DOT Grant No. DTOS59-07-G-00053 awarded by the Department of Transportation. The Government has certain rights in this invention.

BACKGROUND

Butanol is a drop-in fuel, which in many cases is more desirable than ethanol due to its higher energy density and compatibility with existing fuel infrastructure (Fortman et al., 2008; Wang et al., 2009). Butanol can be converted with a hydrogenation step to drop-in diesel and jet fuels (Simmons, 2011; Yang and Wyman, 2008).

Butanol has been produced by the traditional acetone-butanol-ethanol (ABE) fermentation using molasses and starches (Jones and Woods, 1986; Ni and Sun, 2009), and recently from lignocellulosic biomass (Liu et al., 2015a; Liu et al., 2015b; Qureshi et al., 2010). Unfortunately, the yield of butanol from biomass conversion is poor because a large amount of the biomass is used by solventogenic *Clostridium* species for the production of un-captured $CO_2$ and $H_2$. During butanol production via ABE fermentation, more than 50% of the carbon from sugars is wasted in producing $H_2$ and $CO_2$ (Zhu and Yang, 2010). Most of these gas byproducts are released into the atmosphere, leaving a negative impact on process economy. Therefore, it is critical to improve ABE yields from renewable sources to make this process viable.

Thus, the present disclosure is directed to new and improved biocatalytic conversion systems and methods of producing and using same that have improved yields and thus overcome the disadvantages and defects of the prior art.

DETAILED DESCRIPTION

Figure 1:
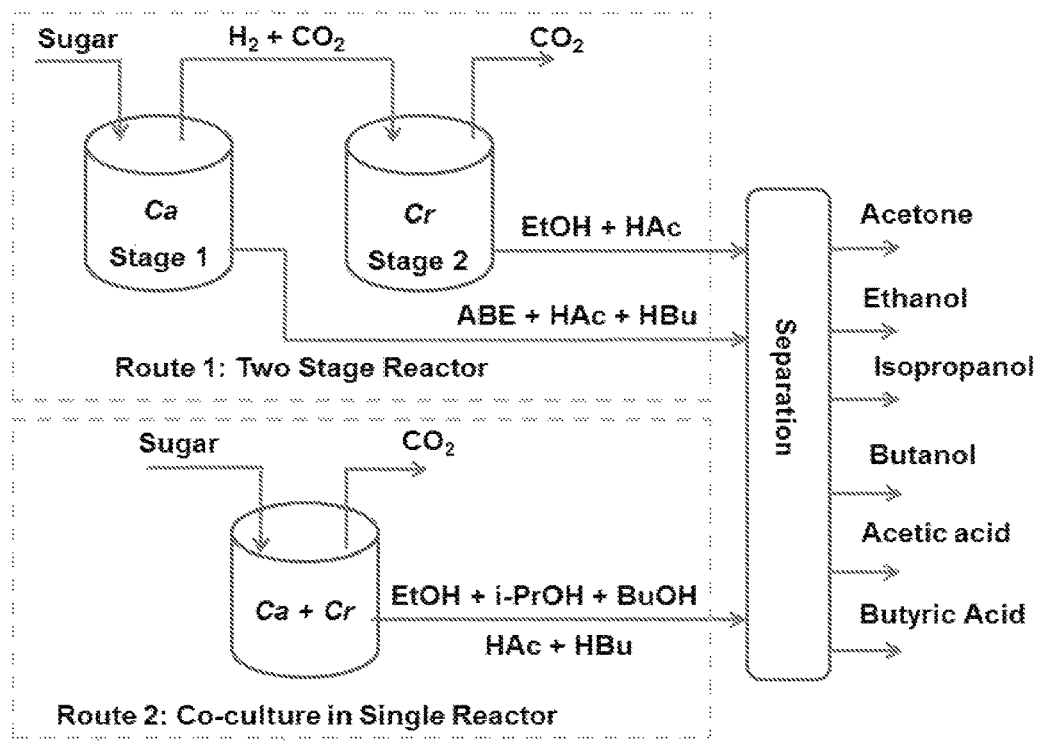
FIG. 1 is a schematic diagram of an embodiment of a co-fermentation system in two stage reactor and co-culture in one stage reactor with an example of bacteria (Ca: *Clostridium acetobutylicum* and Cr: *Clostridium ragsdalei*) and possible products that can be made. ABE: acetone-butanol-ethanol; EtOH: ethanol; i-PrOH: isopropanol; BuOH: butanol; HAc: acetic acid; and HBu: butyric acid.

Before explaining at least one embodiment of the inventive concept(s) in detail by way of exemplary language and results, it is to be understood that the inventive concept(s) is not limited in its application to the details of construction and the arrangement of the components set forth in the following description. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed inventive concept(s) shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses and chemical analyses.

All patents, published patent applications, and non-patent publications mentioned in the specification are indicative of the level of skill of those skilled in the art to which this presently disclosed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions and/or methods disclosed herein can be made and executed without undue experimentation in light of the present disclosure. While the compositions and methods of the inventive concept(s) have been described in terms of particular embodiments, it will be apparent to those of skill in the art that variations may be applied to the compositions and/or methods and in the steps or in the sequence of steps of the methods described herein without departing from the concept, spirit, and scope of the inventive concept(s). All such similar substitutions and modifications apparent to those skilled in the art are deemed to be within the spirit, scope, and concept of the inventive concept(s) as defined by the appended claims.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, three or more compounds, four or more compounds, or greater numbers of compounds. The term "plurality" refers to "two or more."

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order or importance to one item over another or any order of addition, for example.

For purposes of the instant disclosure, the term "at least" followed by a number is used herein to denote the start of a range beginning with that number (which may be a ranger having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Similarly, it is to be understood that where the specification states that a component, feature, structure, or characteristic "may," "might," "can," or "could" be included, that particular component, feature, structure, or characteristic, while present in one or more particular (but non-limiting) embodiments, is not required to be included in all embodiments.

Throughout this application, the term "about" is used to indicate that a value includes the inherent variation of error for a composition/apparatus/device, the method being employed to determine the value, or the variation that exists among the study subjects. For example, but not by way of limitation, when the term "about" is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent from the specified value, as such variations are appropriate to perform the disclosed methods and as understood by persons having ordinary skill in the art.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. For example, the term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

As used herein, "substantially pure" means an object species is the predominant species present (i.e., on a molar basis it is more abundant than any other individual species in the composition), and a substantially purified fraction is a composition wherein the object species comprises at least about 50 percent (on a molar basis) of all macromolecular species present. Generally, a substantially pure composition will comprise more than about 80 percent of all macromolecular species present in the composition, such as (but not limited to) more than about 85%, 90%, 95%, and 99%. In a particular (but non-limiting) embodiment, the object species is purified to essential homogeneity (contaminant species cannot be detected in the composition by conventional detection methods), wherein the composition consists essentially of a single macromolecular species.

When, in this document, a range is given as "(a first number) to (a second number)" or "(a first number)-(a second number)," this means a range whose lower limit is the first number and whose upper limit is the second number. For example, 25 to 100 should be interpreted to mean a range whose lower limit is 25 and whose upper limit is 100. Additionally, it should be noted that where a range is given, every possible subrange or interval within that range is also specifically intended unless the context indicates to the contrary. For example, if the specification indicates a range of 25 to 100, such range is also intended to include subranges such as 26-100, 27-100, etc., 25-99, 25-98, etc., as well as any other possible combination of lower and upper values within the stated range, e.g., 33-47, 60-97, 41-45, 28-96, etc. Note that integer range values have been used in this paragraph for purposes of illustration only, and decimal and fractional values (e.g., 46.7-91.3) should also be understood to be intended as possible subrange endpoints unless specifically excluded.

Where applicable, although state diagrams, flow diagrams or both may be used to describe embodiments, the present disclosure is not limited to those diagrams or to the corresponding descriptions. For example, flow need not move through each illustrated box or state, or in exactly the same order as illustrated and described.

The term "method," as used herein, may refer to manners, means, techniques, and procedures for accomplishing a given task including, but not limited to, those manners, means, techniques, and procedures either known to, or readily developed from known manners, means, techniques, and procedures by practitioners of the art to which the present disclosure belongs.

Methods of the present disclosure may be implemented by performing or completing manually, automatically, or a combination thereof, selected steps or tasks. In addition, unless otherwise indicated, the selected steps or tasks of each method may be performed simultaneously or wholly or partially sequentially. In addition, unless indicated otherwise, the order and sequence of selected steps or tasks of each method are for purposes of illustration only; changes may be made in the order and sequence of steps, so long as the method is capable of functioning in accordance with the present disclosure. That is, where reference is made herein to a method comprising two or more defined steps, the defined steps can be carried out in any order or simultaneously (except where context excludes that possibility). In addition, any of the methods of the present disclosure can also include one or more other steps which are carried out before any of the defined steps, between two of the defined steps, or after all of the defined steps (except where context excludes that possibility).

Turning now to the inventive concept(s), disclosed herein are biocatalytic conversion systems and methods of producing and using same, particularly (but not limited to), in the production of at least one alcohol, at least one ketone, and/or at least one organic acid.

Certain non-limiting embodiments are directed to a biocatalytic conversion system that utilizes a co-fermentation process for sugar and gaseous substrates. The biocatalytic conversion system comprises two reactors with a gas line connecting the two. The first reactor comprises at least one fermentation medium containing at least one first microorganism. The at least one fermentation medium comprises at least one sugar substrate, and the at least one first microorganism comprises a sugar fermenting species that converts sugars into at least one of acetone, butanol, ethanol, isopropanol, acetic acid, and butyric acid. In addition, a gaseous substrate comprising $CO_2$ and $H_2$ gases is produced during the fermentation process. The second reactor comprises at least one medium containing at least one second microorganism, wherein the at least one second microorganism comprises a gas fermenting species that converts $CO_2$ and $H_2$ gases into at least one of an alcohol and an organic acid. The gas line connects the first reactor to the second reactor for feeding the gaseous substrate produced in the first reactor into the second reactor. For example (but not by way of limitation), the gas line may connect a headspace of the first reactor to a headspace of the second reactor. Alternatively, gas transferred from the first reactor can be bubbled into the liquid medium of the second reactor.

Certain non-limiting embodiments of the present disclosure are also directed to a biocatalytic conversion system that utilizes a co-fermentation process for sugars and gases. These embodiments are similar to the biocatalytic conversion system above except that all components are placed within a single reactor. That is, the biocatalytic conversion system comprises a reactor that includes at least one fermentation medium and two species of microorganisms. The at least one fermentation medium comprises at least one sugar substrate. The at least one first microorganism comprises a sugar fermenting species that converts sugars into at least one of acetone, butanol, ethanol, isopropanol, acetic acid, and butyric acid, and wherein a gaseous substrate comprising $CO_2$ and $H_2$ gases is produced during the fermentation process. The at least one second microorganism comprises a gas fermenting species that converts $CO_2$ and $H_2$ gases produced during the fermentation of sugars into at least one of an alcohol and an organic acid.

In a particular (but non-limiting) embodiment, the biocatalytic conversion systems disclosed or otherwise contemplated herein produce at least one alcohol, at least one ketone, and at least one organic acid.

Certain non-limiting embodiments of the present disclosure are directed to a method of biocatalytic conversion that utilizes a co-fermentation process for sugar and gaseous substrates. The method comprises the steps of: (a) contacting at least one fermentation medium with at least one first microorganism in a first reactor, wherein the at least one fermentation medium comprises at least one sugar substrate, and wherein the at least one first microorganism converts the at least one sugar substrate into at least one of acetone, butanol, ethanol, isopropanol, acetic acid, and butyric acid, and wherein a gaseous substrate comprising $CO_2$ and $H_2$ gases is produced during the fermentation process; and (b) feeding the gaseous substrate produced in the first reactor into a second reactor, the second reactor comprising at least one medium containing at least one second microorganism, wherein the at least one second microorganism converts $CO_2$ and $H_2$ gases into at least one of an alcohol and an organic acid.

Certain non-limiting embodiments of the present disclosure are directed to a method of biocatalytic conversion that utilizes a co-fermentation process for sugar and gaseous substrates. The method comprising the steps of: (a) contacting at least one fermentation medium with at least one first microorganism in a reactor, wherein the at least one fermentation medium comprises at least one sugar substrate, and wherein the at least one first microorganism converts the at least one sugar substrate into at least one of acetone, butanol, ethanol, isopropanol, acetic acid, and butyric acid, and wherein a gaseous substrate comprising $CO_2$ and $H_2$ gases is produced during the fermentation process; and (b) contacting the gaseous substrate produced during the fermentation process with at least one second microorganism present in the reactor, wherein the at least one second microorganism converts $CO_2$ and $H_2$ gases produced during the fermentation of sugars into at least one of an alcohol and an organic acid.

Any biocatalytic species (or combinations thereof) that are known in the art or otherwise contemplated herein and that can function in accordance with the present disclosure are included within the scope of the systems and methods described herein. That is, any type of saccharolytic species, or any co-culture or mixed culture containing one or more saccharolytic species, may be utilized as the at least one first microorganism. Likewise, any microbial catalyst capable of fermenting synthesis gas ("syngas," which typically comprises CO, $CO_2$, and $H_2$) to produce one or more liquid biofuels or chemicals, as well as any co-culture or mixed culture containing one or more of said microbial catalysts, may be utilized as the at least one second microorganism.

In certain particular (but non-limiting) embodiments, each of the first and second microorganisms comprises one or more individual species of microorganisms, wherein each individual species is from a genus selected from the group consisting of *Clostridium, Butyribacterium, Eubacterium, Moorella, Acetobacterium, Enterobacter, Bacillus, Anaerobaculum, Alkalibaculum*, and combinations thereof. For example, but not by way of limitation, the at least one first microorganism may comprise at least one of *Clostridium acetobutylicum, Bacillus firmus, Anaerobaculum hydrogeniformans*, and *Clostridium beijerinckii*. In another non-limiting example, the at least one second microorganism may comprise at least one of *Clostridium ragsdalei, Clostridium autoethanogenum, Clostridium carboxidivorans, Clostridium ljungdahlii*, and *Alkalibaculum bacchi*.

In a particular (but non-limiting) embodiment, each of the first and second microorganisms comprises a *Clostridium* species, and each of the first and second microorganisms may contain a mono-culture or a co-culture/mixed culture containing said *Clostridium* species. A particular (but non-limiting) example of bacteria that may be utilized as the at least one first microorganism comprises *Clostridium acetobutylicum* ATCC 824 (including a co-culture or mixed culture containing same). A particular (but non-limiting) example of bacteria that may be utilized as the at least one second microorganism comprises *Clostridium ragsdalei* P11 (including a co-culture or mixed culture containing same).

When the at least one second microorganism comprises *Clostridium ragsdalei* (including a co-culture or mixed culture containing same), ethanol, acetic acid, and isopropanol can be produced in the reactor containing the at least one second microorganism. When the at least one second microorganism comprises *Clostridium carboxidivorans* (including a co-culture or mixed culture containing same), ethanol, butanol, hexanol, butyric acid, acetic acid, and hexanoic acid can be produced in the reactor containing the at least one second microorganism.

Any fermentation media that can support the functions of the first and/or second microorganisms can be utilized in accordance with the systems and methods of the present disclosure. In certain non-limiting embodiments, the sugar substrate present in the fermentation medium is selected from the group consisting of glucose, fructose, sucrose, xylose, galactose, arabinose, mannose, and combinations thereof. However, other sugar substrates that can be broken down by microorganisms can also be utilized in accordance with the present disclosure.

In certain non-limiting embodiments, the fermentation medium contains a pure (or substantially pure) sugar for use in the production of alcohol(s), ketone(s), and/or organic acid(s). Alternatively, the fermentation may contain any type of material that can comprise one or more sugars for use in the production of alcohol(s), ketone(s), and/or organic acid (s). In certain non-limiting embodiments, the fermentation medium comprises at least one raw material selected from the group consisting of a sugar, a starch, cellulose, hemicellulose, other carbohydrates, glucan, xylan, galactan, mannan, cellobiose, other carbohydrates, lignocellulosic biomass (such as, but not limited to, grasses and wood materials), wastes containing lignocellulosic materials, and combinations thereof. In certain non-limiting embodiments, the fermentation medium contains a feedstock selected from the group consisting of switchgrass, forage sorghum, redcedar, woody materials, and combinations thereof. When a feedstock is present in the fermentation medium, the feedstock may be pretreated and hydrolyzed prior to placement in the fermentation medium, so as to release sugars for fermentation.

The medium fed into the reactor containing the at least one first microorganism may contain any concentration of sugar and/or feedstock, so long as the biocatalytic conversion system is capable of functioning as described herein to produce one or more products (including, but not limited to, one or more of acetone, butanol, ethanol, isopropanol, acetic acid, butyric acid, as well as one or more other alcohols and/or organic acids) with any level of yield. For example (but not by way of limitation), the feedstock may be present in the medium in a concentration of at least about 0.01%, at least about 0.05%, at least about 0.1%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, and at least about 99%. In addition, the scope of the presently disclosure also includes the presence of feedstock in the medium at any percent yield that falls within any range formed from the combination of two values listed above (for example, a range of from about 10% to about 99%, a range of from about 30% to about 98%, a range of from about 50% to about 97%, a range of from about 60% to about 96%, a range of from about 70% to about 95%, etc.).

The reactors utilized in the biocatalytic conversion systems disclosed herein may be maintained at any temperature and any pH that allows the reactors to perform as described or otherwise contemplated herein. In a particular (but non-limiting) embodiment, when two reactors are present in the biocatalytic conversion system, the first reactor is maintained at a temperature in a range of from about 20° C. to about 45° C., such as (but not limited to) about 37° C., while a pH of the at least one fermentation medium present in the first reactor is maintained in a range of from about 4.0 to about 7.5, such as (but not limited to) between about 6.5 and about 6.8. Also in this particular (but non-limiting) embodiment, the second reactor is maintained at a temperature in a range of from about 20° C. to about 45° C., such as (but not limited to) about 37° C., while a pH of the at least one fermentation medium present in the second reactor is maintained in a range of from about 4.0 to about 7.5, such as (but not limited to) about 6.0. The use of thermophilic microorganisms in the biocatalytic conversion system requires a higher temperature range of from about 20° C. to about 65° C., such as (but not limited to) about 55° C. In another particular (but non-limiting) embodiment, when a single reactor is present in the biocatalytic conversion system, the one reactor is maintained at a temperature in a range of from about 20° C. to about 45° C., such as (but not limited to) about 37° C., while a pH of the at least one fermentation medium present in the reactor is maintained in a range of from about 4.0 to about 7.5, such as (but not limited to) about 6.5.

In certain particular (but non-limiting) embodiments, the biocatalytic conversion systems and methods of the present disclosure may further include the addition of an external gas feed into the reactor containing the at least one second microorganism. For example (but not by way of limitation), external CO and/or $H_2$ gas may be fed into the single reactor system or into the second reactor of a two reactor system.

Each of the systems and methods disclosed or otherwise contemplated herein may be performed in batch reactions or via fed-batch or continuous flow methodologies. That is, the systems and methods may include the use of batch reactors or continuous flow reactors.

Each of the systems or methods described or otherwise contemplated herein can produce one or more products (including, but not limited to, one or more of acetone, butanol, ethanol, isopropanol, acetic acid, butyric acid, as well as one or more other alcohols and/or organic acids) with any level of yield. For example (but not by way of limitation), the one or more products can be produced with a yield of at least about 0.01%, at least about 0.05%, at least about 0.1%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, and at least about 99%. In addition, the scope of the presently disclosure also includes the production of one or more products at any percent yield that falls within any range formed from the combination of two values listed above (for example, a range of from about 10% to about 99%, a range of from about 30% to about 98%, a range of from about 50% to about 97%, a range of from about 60% to about 96%, a range of from about 70% to about 95%, etc.).

In particular (but not by way of limitation), there is provided herein an embodiment of an integrated conversion process that uses a novel co-fermentation process (see FIG. 1). One non-limiting objective of the present disclosure is to establish an integrated novel conversion process for production of butanol and other alcohols utilizing novel biocatalytic conversion processes. Various embodiments can be performed in one reactor in a co-culture/mixed culture, or in two reactors as separate cultures (including two separate mono-cultures, co-cultures, and/or mixed cultures) to produce various products (FIG. 1). Various feedstocks containing sugars, starch, cellulose, hemicellulose, and/or other carbohydrates can be used in the present disclosure. Some of the feedstocks should be processed first to release the sugars to be used by the biocatalyst in the present disclosure. Existing methods to release sugars from starch and lignocellulosic feedstocks can be used; as these methods are well known in the art, no further description thereof is deemed necessary.

According to one particular (but non-limiting) embodiment, there is provided a process that consists of a co-fermentation of sugars and gaseous substrates for ABE production in a single fermentation system while converting $CO_2$ and $H_2$ to alcohols and organic acids, thus adding extra revenue to biorefineries. The raw materials can be starch and sugar crops or lignocellulosic biomass. Depending on the microorganisms and reactor configuration used, an embodiment can enhance alcohol yield by more than 25%. In one example, the use of two-stage reactors resulted in a 19% improvement in ABE yield from sugar conversion by *C. acetobutylicum* ATCC 824 in the first stage and conversion of $H_2$ and $CO_2$ by *C. ragsdalei* in the second reactor. The total organic acid production in the co-fermentation process in the two-stage reactors was also increased by 141% due to conversion of $H_2$ and $CO_2$. In addition to reducing $CO_2$ emissions, the co-fermentation of sugars and gases has the potential to enhance the feasibility of ABE fermentation by producing more alcohols from generated waste gas streams.

Various feedstocks containing sugars, starch, cellulose, hemicellulose, and/or other carbohydrates can be used in the present disclosure. Some of the feedstocks may need to be processed first to release the sugars to be used by the biocatalyst in the present disclosure. Existing methods to release sugars from starch and lignocellulosic feedstocks can be used; as these methods are well known in the art, no further description thereof is deemed necessary.

Examples of feedstocks that can be used include (but are not limited to) switchgrass, forage sorghum, redcedar, and woody materials. Pretreated switchgrass and redcedar will be hydrolyzed using commercial enzymes to release the sugars for the fermentation process. After hydrolysis of pretreated biomass, the fermentation process can proceed in two routes according to the embodiments shown in FIG. 1. In Route 1 (two stage reactor), the released sugars are fermented in the first reactor using at least one first microorganism (such as, but not limited to, a mono-culture of *Clostridium acetobutylicum*) to acetone, butanol, and ethanol (ABE), and the generated $H_2$ and $CO_2$ are fermented in the second reactor by a at least one second microorganism (such as, but not limited to, *Clostridium ragsdalei* or a co-culture or mixed culture of microorganisms containing same) to ethanol and acetic acid. In Route 2 (single reactor), the released sugars and generated $H_2$ and $CO_2$ are converted to isopropanol, butanol, and ethanol (IBE) as well as organic acids using a co-culture or mixed culture of first and second microorganisms (such as, but not limited to, a co-culture comprising *C. acetobutylicum* and *C. ragsdalei*). Butanol is the main product in this process from both routes. However, the process route, microorganisms, and operating conditions utilized affect the product ratios and yields.

Separate hydrolysis and fermentation, simultaneous saccharification and co-fermentation, and other fermentation schemes can be used. *C. acetobutylicum* and *C. ragsdalei* require similar growth medium and conditions for growth such as temperature and pH. *C. acetobutylicum* converts C5 and C6 sugars to ABE, in a typical product ratio of about 3:6:1. *C. ragsdalei*, developed through collaborative efforts between OSU and OU (U.S. Pat. No. 7,704,723, issued to Huhnke et al. on Apr. 27, 2010, the entire contents of which are hereby expressly incorporated herein by reference), converts acetone into isopropanol, organic acids into alcohols, and $H_2$ and $CO_2$ into ethanol and acetic acid. Also, while certain particular species have been described herein, it will be understood that the systems and methods of the present disclosure can be used with any other combination of microorganisms that are capable of converting sugars and $CO/CO_2/H_2$ into various products to support food, agriculture, pharmaceutical, environmental, and energy industries.

The present disclosure is the first report to describe the co-fermentation of sugars and gases for alcohol and organic acid production using pure sugars or sugars derived from biomass.

The foregoing has outlined in broad terms some of the more important features of the present disclosure so that the detailed description that follows may be more clearly understood, and so that the contribution of the instant inventors to the art may be better appreciated. The inventive concept(s) is not to be limited in its application to the details of the construction and to the arrangements of the components set forth in the following description or illustrated in the drawings. Rather, the inventive concept(s) is capable of other embodiments and of being practiced and carried out in various other ways not specifically enumerated herein. Finally, it should be understood that the phraseology and terminology employed herein are for the purpose of description and should not be regarded as limiting, unless the specification specifically so limits the inventive concept(s).

EXAMPLE

Examples are provided hereinbelow. However, the present disclosure is to be understood to not be limited in its application to the specific experimentation, results, and laboratory procedures disclosed herein. Rather, the Examples are simply provided as one of various embodiments and are meant to be exemplary, not exhaustive.

To address the defects and disadvantages of the prior art discussed in detail in the Background section, an integrated conversion process using a novel co-fermentation process has been developed (FIG. 1). Various feedstocks containing sugars, starch, cellulose, hemicellulose, and/or other carbohydrates can be used with the novel co-fermentation process. Some feedstocks should be pretreated and hydrolyzed to release the sugars for fermentation. In addition, separate hydrolysis and fermentation, simultaneous saccharification and co-fermentation, and other fermentation schemes can be used with this process.

In Route 1 of FIG. 1, two reactors are used in series to make ABE products. In the first reactor, sugar fermenting microorganisms such as *Clostridium acetobutylicum* (Ca) or *Clostridium beijerinckii* (Cb) are used to convert sugars into ABE as well as acetic and butyric acids. The $CO_2$ and $H_2$ produced in the first reactor are fed to the second reactor containing gas fermenting microorganisms such as *Clostridium ragsdalei* (Cr) or *Clostridium carboxidivorans* (Cc) to make additional alcohols and organic acids. Route 2 show an example of a co-culture of sugar fermenting microorganism (Ca) and gas fermenting microorganism (Cr) used in one reactor. Route 2 is more desirable than route 1 because it saves more capital and operating costs using one reactor. In this novel process, more ethanol and acetic acid are produced when Cr is used. Also, when Cr is used in Route 2, acetone is converted to isopropanol. However, when Cc is used in Route 2, more butanol and butyric acid are produced. Unlike Cr, Cc does not have the ability to convert acetone to isopropanol (Ramachandriya et al., 2011).

The methods of the present disclosure can also be used with other microorganisms to produce various products benefiting from the co-utilization of sugars and gases. Butanol is the main product in this process from both routes. However, the process route, microorganisms, and operating conditions utilized affect the product ratios and yields. When feasible, the addition of external CO or $H_2$ into the reactor with the gas fermenting microorganism can increase alcohol formation and further reduces $CO_2$ emission.

The current Examples focus on co-fermentation of sugars and gaseous substrates for ABE and organic acid production in a single fermentation system. Therefore, this approach of co-fermentation enhances the process economy by generating extra income utilizing the off-gas streams while also reducing $CO_2$ emissions. Pure sugars and sugars derived from woody biomass (such as, but not limited to, eastern redcedar) were used in the Examples. In particular, in Example 2, the eastern redcedar was used as a feedstock for the co-fermentation process following pretreatment, enzymatic hydrolysis, and detoxification thereof.

Figure 3:
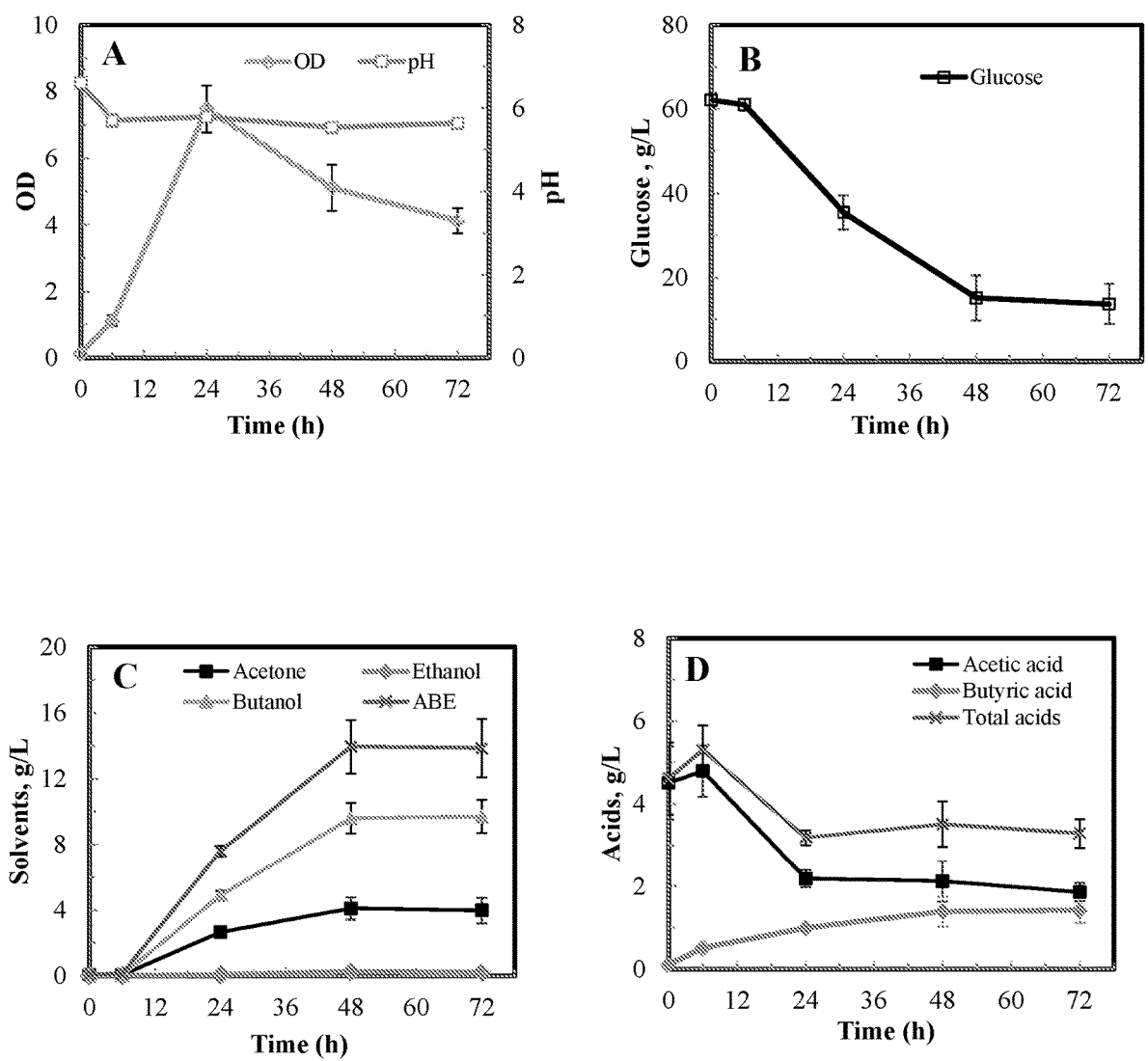
FIG. 3 graphically illustrates (A) Growth and pH, (B) glucose, (C) solvents, and (D) organic acids profiles during ABE fermentation in Fermentor A using *C. acetobutylicum* ATCC 824 with Medium I (pure glucose) (n=3).
Figure 4:
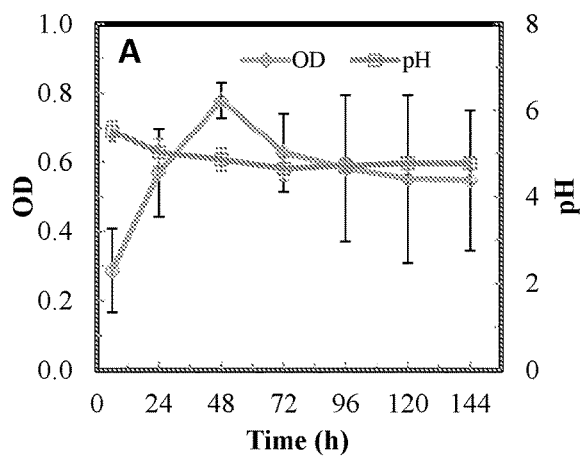
FIG. 4 graphically illustrates (A) Growth and pH, (B) gas consumption/production, (C) ethanol and acetic acid, and (D) absolute headspace pressure profiles during gas fermentation in Fermentor B using *C. ragsdalei* with Medium I (pure glucose) in Fermentor A (n=3).
Figure 4:
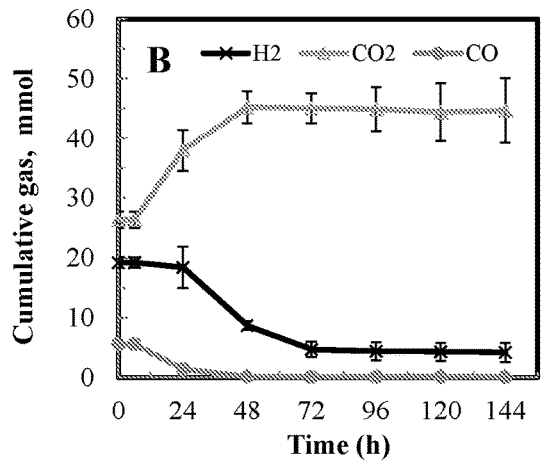
Figure 4:
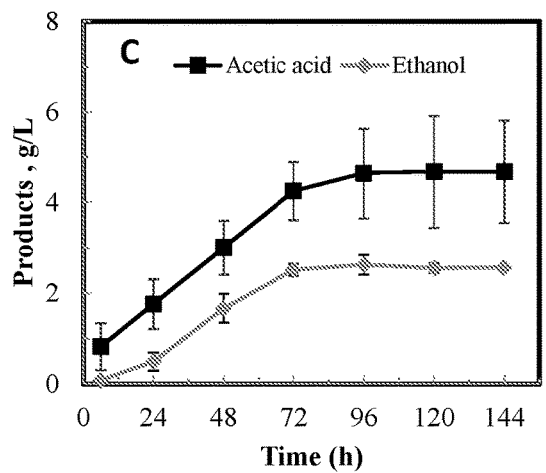
Figure 4:
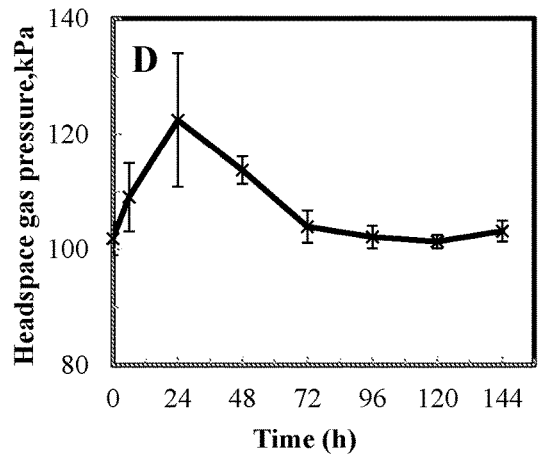

The present disclosure is the first report of co-fermentation of sugars and gases for production of alcohol and organic acids using pure sugars or sugars derived from biomass. For example (but not by way of limitation), the use of *C. acetobutylicum* ATCC 824 and *C. ragsdalei* in two-stage reactors has shown a 19% improvement in ABE (acetone-butanol-ethanol) yield due to additional ethanol produced from $H_2$ and $CO_2$. In addition, total organic acid production in the co-fermentation process increased by 141% due to utilization of $H_2$ and $CO_2$ (FIGS. 3 and 4). In addition to reducing $CO_2$ emissions, the novel co-fermentation of sugars and gases enhances the process economics by producing more products from wasted gas streams.

Example 1—Co-Fermentation of Pure Glucose and Generated $CO_2$ and $H_2$

Methods of Example 1
Microorganisms and Inoculum Preparation

*Clostridium ragsdalei* strain P11 and *Clostridium acetobutylicum* ATCC 824 were used in the study. *C. acetobutylicum* culture was maintained as spore suspension in sterile distilled water at 4° C. (Liu et al., 2015b). Tryptone-glucose-yeast (TGY) medium was used in pre-culturing of *C. acetobutylicum*. The TGY medium contained (per liter): 30 g tryptone, 20 g glucose, 10 g yeast extract, and 1 g of cysteine (Ezeji et al., 2013). The TGY medium was autoclaved for 15 min at 121° C. (PRIMUS, Sterilizer CO. Inc., Omaha, Nebr., USA) with the reactor bottles, tips, and test tubes before the inoculation. The heat shock protocol of *C. acetobutylicum* and inoculation procedures were previously described (Liu et al., 2015b). *C. ragsdalei* was pre-cultured on standard medium that contained (per liter): 1 g yeast extract, 25 mL mineral stock solution, 10 mL vitamin stock solution, 10 mL trace metals stock solution, 10 g N-morpholinoethane-sulfonic acid (MES) buffer, 2.5 mL of 4% cysteine sulfide solution, and 1 mL of 0.1% resazurin solution. The mineral stock solution contained (per liter): 100 g ammonium chloride, 20 g magnesium sulfate, 10 g potassium chloride, 10 g potassium phosphate monobasic, and 4 g calcium chloride. The vitamin stock solution contained (per liter): 10 mg MESNA (2-mercaptoethanesulfonic acid sodium salt), 10 mg pyridoxine, 5 mg p-(4)-aminobenzoic acid, 5 mg calcium pantothenate, 5 mg nicotinic acid, 5 mg riboflavin, 5 mg thiamine, 5 mg thioctic acid, 5 mg vitamin B12, 2 mg d-biotin, and 2 mg folic acid. The trace metal stock solution contained (per liter): 2.0 g nitrilotriacetic acid, 1.0 g manganese sulfate, 1.0 g zinc sulfate, 0.8 g ferrous ammonium sulfate, 0.2 g cobalt chloride, 0.2 g nickel chloride, 0.2 g sodium tungstate, 0.1 g sodium selenate, and 0.02 g sodium molybdate. The pH of $C.$ $ragsdalei$ medium was adjusted during preparation to 6.0 using 5N KOH solution.

Pre-culturing of $C.$ $ragsdalei$ in Passage I was performed in serum bottles containing standard $C.$ $ragsdalei$ medium (45 mL working volume) and 5 mL of seed culture. Then, the culture bottles were flushed for 3 min with synthesis gas (syngas) Mix I, which contained 20% CO, 15% $CO_2$, 5% $H_2$, and 60% $N_2$, by volume. The bottles were pressurized to 170.2 kPa (abs) with syngas Mix I and stored in a warm room (37° C.) without agitation. After two days, the bottles were placed on a shaker at 150 rpm and 37° C. Once the optical density (OD) of culture in Passage I reached 0.5 units, the culture from Passage I was used to inoculate fresh medium in Passage II for further adaptation to higher levels of CO, $CO_2$, and $H_2$. The gas composition used in Passage II was syngas Mix II containing 40% CO, 30% $CO_2$, and 30% $H_2$, by volume. Passage II bottles were flushed with syngas Mix II for 3 min prior to inoculation of $C.$ $ragsdalei$ from Passage I. After inoculation, Passage II bottles were pressurized to 239.1 kPa (abs) with syngas Mix II and placed on a shaker at 150 rpm and 37° C. Once the OD in Passage II bottles reached about 1 OD unit (usually within 24 to 36 h), this culture was used to inoculate the gas fermentor (Fermentor B) in FIG. 2.

Reactor Configuration

Figure 2:
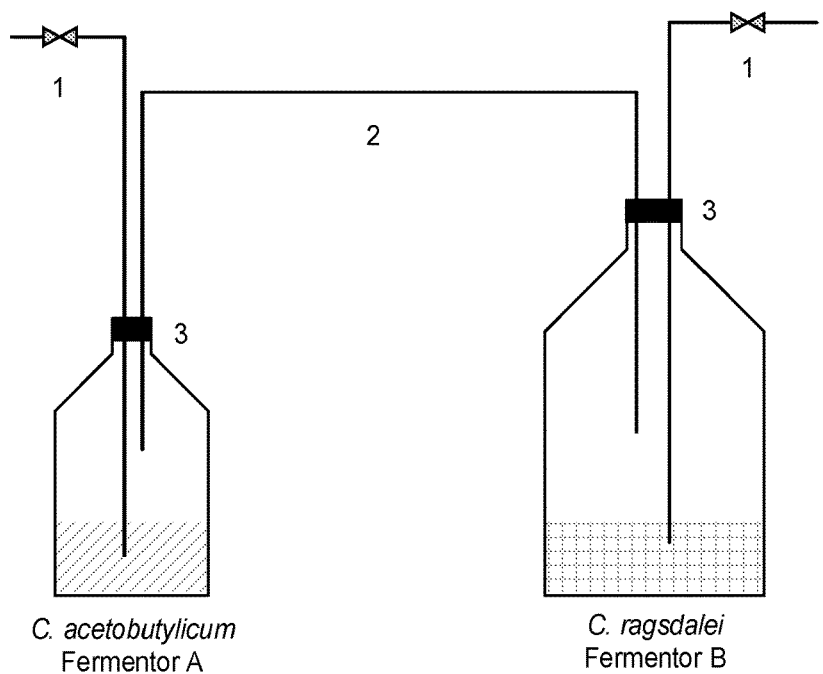
FIG. 2 contains an exemplary schematic diagram of co-fermentation of sugars in Fermentor A and $CO_2$ and $H_2$ in Fermentor B. 1: valves for sampling liquid; 2: gas line; and 3: rubber stopper for sealing and gas sampling.

The co-fermentation system consisted of a 250 mL (Fermentor A for $C.$ $acetobutylicum$) and a 1-L (Fermentor B for $C.$ $ragsdalei$) Corning glass bottles with rubber stoppers to maintain the gastight operation (FIG. 2). The headspaces of Fermentors A and B were connected with ⅛" inner diameter stainless steel tubing. Similar diameter tubing with two valves was used to obtain liquid samples from both fermentors. The headspace in the two fermenters before inoculation contained 10% CO, 52.2% $CO_2$, and 37.8% $H_2$, by volume, at 101.3 kPa (abs). After inoculation, Fermentor B was kept on a magnetic stirrer, and the stirring speed was maintained at 150 rpm. The initial working volume in each of Fermentor A and Fermentor B was 50 mL.

Fermentation Medium

ABE fermentations was performed in Fermentor A using two medium formulations. Medium I (used in Example 1) was a pure sugar medium, and Medium II (used in Example 2) contained detoxified redcedar hydrolyzate. Medium I consists of P2 medium and 60 g/L glucose and about 2 g/L xylose. Medium II contained P2 medium and redcedar hydrolyzate with similar glucose and xylose concentrations as in Medium I. Pre-culturing of $C.$ $acetobutylicum$ (ATCC 824) was carried out with TGY medium as discussed in the "Microorganisms and inoculum preparation" section. Medium I was autoclaved at 121° C. for 15 min and cooled down to 40° C. prior to transfer into the anaerobic chamber. Medium I was then transferred into pre-sterile loosely capped 250 mL Fermentor A and supplemented with 2% (v/v) of pre-sterile yeast extract (50 g/L), 5% (v/v) of 1M acetate buffer solution at pH 5.5, and 1% (v/v) of P2 vitamin, buffer, and trace metal solutions. Prior to inoculation, the pH of Medium I was adjusted to between 6.5 and 6.8 using 2N KOH. Medium I was then inoculated with 6% (v/v) actively growing $C.$ $acetobutylicum$ pre-cultured in TGY medium. Medium II contained P2 vitamin, buffer, and trace metal solutions, and redcedar hydrolyzate. The redcedar hydrolyzate was diluted to achieve a glucose concentration of 60 g/L in Medium II. No pH adjustment was required during Medium II preparation.

Conversion of $CO_2$ and $H_2$ occurred in Fermentor B. Standard $C.$ $ragsdalei$ medium was used as described in the "Microorganisms and inoculum preparation" section. Prior to inoculation, about 60% (v/v) of fresh sterile $C.$ $ragsdalei$ medium was added into Fermentor B. A 4% cysteine sulfide solution at 0.25% (v/v) was then added to deoxygenate and reduce the medium. Then 40% (v/v) of actively growing $C.$ $ragsdalei$ pre-culture from Passage II was transferred aseptically into Fermentor B at 6 hours after starting ABE fermentation in Fermentor A. Both Fermentors A and B were maintained at 37° C.

Analytical Methods

During fermentation, 1 mL liquid samples from Fermentors A and B were aseptically taken at various times to determine cell growth, pH, and product profiles. The optical density (OD) of the fermentation medium from the liquid samples from Fermentors A and B were determined using a UV spectrophotometer (UV-2100) at 600 nm and 660 nm, respectively. Sugar concentration in Fermentor A was analyzed using a HPLC (HPLC1200, Agilent Technologies, Wilmington, Del., USA). However, solvents, ketones, and organic acids produced in Fermentors A and B were measured using GC-FID (GC 6890, Agilent Technologies, Wilmington, Del., USA) as previously described (Liu et al., 2012; and Ramachandriya et al., 2013). The gas samples from headspaces of each fermentor were analyzed using GC-TCD (Liu et al., 2012).

Results and Discussion of Example 1

Co-Fermentation of Pure Glucose and Generated $CO_2$ and $H_2$

Results of co-fermentation of pure sugars in Medium I by $C.$ $acetobutylicum$ (ATCC 824) and the generated $CO_2$ and $H_2$ by $C.$ $ragsdalei$ are shown in FIGS. 3 and 4. The OD of $C.$ $acetobutylicum$ culture increased to about 7.5 units, while the pH dropped from 6.6 to 5.6 (FIG. 3, Panel A). The pH of Medium I in Fermentor A was not adjusted. After 72 h of fermentation, 48.5 g/L of glucose was consumed by $C.$ $acetobutylicum$ (FIG. 3, Panel B). Fermentation results showed that 9.7 g/L of butanol, 13.9 g/L of total ABE, and 3.3 g/L of total acids were produced (FIG. 3, Panels C and D).

On the other hand, $C.$ $ragsdalei$ grew in Fermentor B on $H_2$ and $CO_2$ and reached a maximum OD of 0.8 while producing 2.6 g/L of ethanol from the off gases ($H_2$ and $CO_2$) produced from Fermentor A (FIG. 4, Panels A and C). Fermentor B produced about 19% additional solvent compared to total ABE produced in Fermentor A. Further, the total acids production in Fermentor B was 4.7 g/L. Total organic acid concentration in both Fermentors increased by 141% due to $H_2$ and $CO_2$ utilization by $C.$ $ragsdalei$. Therefore, the total ABE and organic acids produced from both Fermentors A and B were 16.5 g/L and 8.0 g/L, respectively.

FIG. 4 shows the cumulative production/consumption of different gas components ($H_2$, $CO_2$, and CO). The $H_2$ and $CO_2$ conversion efficiencies during pure glucose fermentation were 72% and 16%, respectively. Further, the $CO_2$ accumulation in the co-fermentation system confirms the production of $CO_2$ is out competed by its consumption due to insufficient availability of reductant gases generated during ABE fermentation. The addition of more $H_2$ or CO in Fermentor B is expected to increase the $CO_2$ conversion to ethanol and acetic acid.

Example 2—Co-Fermentation of Detoxified Redcedar Hydrolyzate and Generated $CO_2$ and $H_2$ Methods of Example 2

The methods of Example 2 were performed as described above in Example 1, with the additional methods described herein below.

Redcedar Pretreatments

Redcedar biomass pretreatment was performed in a 1.0 L Parr reactor (Parr series 4525, Parr Instrument Company, Moline, Ill.). The reactor was equipped with a pressure gauge, heater, an agitator, and a controlling module. According to the particle size distribution (Table 1), 98.5% of the particles were ≤2.0 mm. The amount of redcedar biomass in each pretreatment experiment was determined based on the initial moisture content of the biomass samples. During pretreatment, a 100.0 g of dry redcedar biomass was impregnated at 90° C. for 3.0 h in pretreatment liquor consisting of 3.75 g of sulfuric acid and 20.0 g of sodium bisulfite. In this case, the ratio of pretreatment liquor to biomass was maintained at 5:1 (v/w). Immediately after the 3.0 h of impregnation, the temperature of the reactor was increased to 200° C. and maintained for 10 min (Ramachandriya et al., 2013). The internal pressure of the reactor was recorded separately to confirm the repeatability of the pretreatment process. Immediately after 10.0 min of temperature holding time, the reactor was immersed in an ice bath with manually agitation of the pretreated biomass liquor until the temperature of the reactor dropped to 55° C. After cooling the reactor below 55° C., the solids were separated by vacuum filtration. Subsequently, the filtered wet solids were washed and filtered four times using 500 mL of preheated-deionized water at 60° C. The washed, pretreated redcedar biomass was then stored at 4° C. for further use. The composition of pretreated redcedar was measured as per the National Renewable Energy Laboratory (NREL) protocols (Sluiter et al., 2008).

Enzymatic Hydrolysis

Pretreated redcedar solids were subjected to enzymatic hydrolysis to further breakdown the biomass structure to obtain sugars. ACCELLERASE® 1500 cellulase enzyme complex (Genencor Inc., Palo Alto, Calif., USA) was used. Experiments were performed in 250 mL Erlenmeyer flasks with a total weight of 100 g (including pretreated biomass, water, and enzyme) in each flask and with shaking in an incubator shaker (MaxQ 4450, Thermos Scientific, Dubuque, Iowa, USA) at 250 rpm. A solid loading of 14% was selected in order to obtain 60 g/L glucose for ABE fermentation. The enzyme loading was 50 FPU/g of glucan as previously used (Liu et al., 2015b). A sample of 2.0 mL was taken aseptically from each flask at 6, 12, 24, and 48 h to measure sugar yield.

Detoxification of Enzymatic Hydrolysis

Once the enzymatic hydrolysis was completed (after 48 h), the hydrolyzed redcedar slurry was centrifuged (Avanti J-E, Beckman Coulter, Inc., Brea, Calif., USA) for 15 min at 48,000 g and 4° C. to separate the solids. The centrifugation was continued four times to separate suspended redcedar solids from liquid hydrolyzate before detoxification. The soluble lignin content (SLC) was measured as previously described by Mussatto and Roberto (2006), and bisulfite content was measured as previously described by Liu et al. (2015b) before and after the detoxification of hydrolyzate. Detoxification was performed to remove phenolic inhibitors from the hydrolyzate with 10% (w/v) powdered activated carbon (Hydrodarco B, CABOT, Norit American Inc., Marshall, Tex., USA) (Liu et al., 2015b). The activated carbon was mixed with the hydrolyzate at 250 rpm and 28° C. for 1 h. The activated carbon was then removed from the hydrolyzate by centrifugation at 48,000 g and 4° C. for 15 min. After centrifugation, the hydrolyzate was filter-sterilized using 0.2 µM nylon filters (NALGENE® RAPID-FLOW® filter units, ThermoFisher, Waltham, Mass., USA) and stored in −20° C. freezer for further use.

Results and Discussion of Example 2

Pretreatment of Redcedar Biomass

The redcedar used in the present Example has various particle sizes; thus, a particle size distribution analysis was performed prior to the pretreatment (Table 1). About 1.5% of the total redcedar particles were larger than 2.0 mm. However, 11.3% of the particles were retained in 0.25 mm sieve opening. Nearly 40% of the particles were retained in 1.0 mm sieve. Over 85% of redcedar particle size was between 0.25 mm and 2.0 mm.

Acid-bisulfite pretreatment plays an important role of breaking down the redcedar biomass structure and exposing cellulose and hemicellulose for enzymatic hydrolysis. After the acid-bisulfite pretreatment, seven pretreated redcedar biomass samples were mixed before enzymatic hydrolysis. According to the compositional analysis, the mixed pretreated redcedar biomass contained 53.53±0.34% of glucan, 2.55±0.04% of xylan, 1.33±0.03% of galactan, 2.38±0.16% of mannan, and 32.91±1.14% of lignin.

TABLE 1

Particle size distribution of the redcedar used in the study

| Sieve size (mm) | Mass percent retained on screen (%) |
| --- | --- |
| >2.0 | 1.5 ± 0.1 |
| 2.0 | 16.3 ± 1.3 |
| 1.0 | 38.4 ± 1.7 |
| 0.85 | 8.7 ± 0.1 |
| 0.6 | 10.6 ± 0.3 |
| 0.355 | 8.7 ± 0.4 |
| 0.25 | 4.5 ± 0.7 |
| <0.25 | 11.3 ± 1.6 |

Enzymatic Hydrolysis and Detoxification

Enzymatic hydrolysis of pretreated redcedar was performed using ACCELLERASE® 1500 cellulase enzyme complex (Genencor Inc., Palo Alto, Calif., USA). The final glucose concentration was 73.8 g/L after 48 h of hydrolysis, with a conversion efficiency of 88.6%. The hydrolyzate also contained 1.19±0.02 g/L cellobiose, 2.06±0.02 g/L xylose, 0.22±0.01 g/L galactose, and 0.91±0.01 g/L combined arabinose and mannose concentrations. The pH of the hydrolyzate decreased from 4.85 to 4.76 during the hydrolysis.

Detoxification was used to remove inhibitors and the soluble lignin from the redcedar hydrolyzate before ABE fermentation. The soluble lignin content (SLC) of the hydrolyzate prior to detoxification was 8.59 g/L. After detoxification with activated carbon, the SLC of the detoxified hydrolyzate was reduced to 2.69 g/L. The hydrolyzate was then filtered through a sterile filtration system followed by measuring the SLC of the sterile hydrolyzate. The SLC of the filtered hydrolyzate was 0.74 g/L. Detoxification and filter sterilization reduced the SLC of the hydrolyzate by 91%. In a previous study, the SLC of switchgrass was reduced by 97% after detoxification and filter sterilization (Liu et al., 2015a). It was reported that a SLC above 1.77 g/L inhibited ABE fermentation (Wang and Chen, 2011). In the present study, glucose concentration of the filter sterile hydrolyzate was 70 g/L, which was diluted to 60 g/L in Medium II.

Sodium Bisulfite used in the pretreatment has an antibacterial effect which inhibited the bacterial growth in ABE fermentation (Liu et al., 2015b). Therefore, it is important to measure the bisulfite levels of the hydrolyzate after the biomass pretreatment process and prior to the fermentation. A reduction in bisulfate concentration in the hydrolyzate from 160 to 20 ppm was achieved after detoxification with powdered activated carbon.

Figure 5:
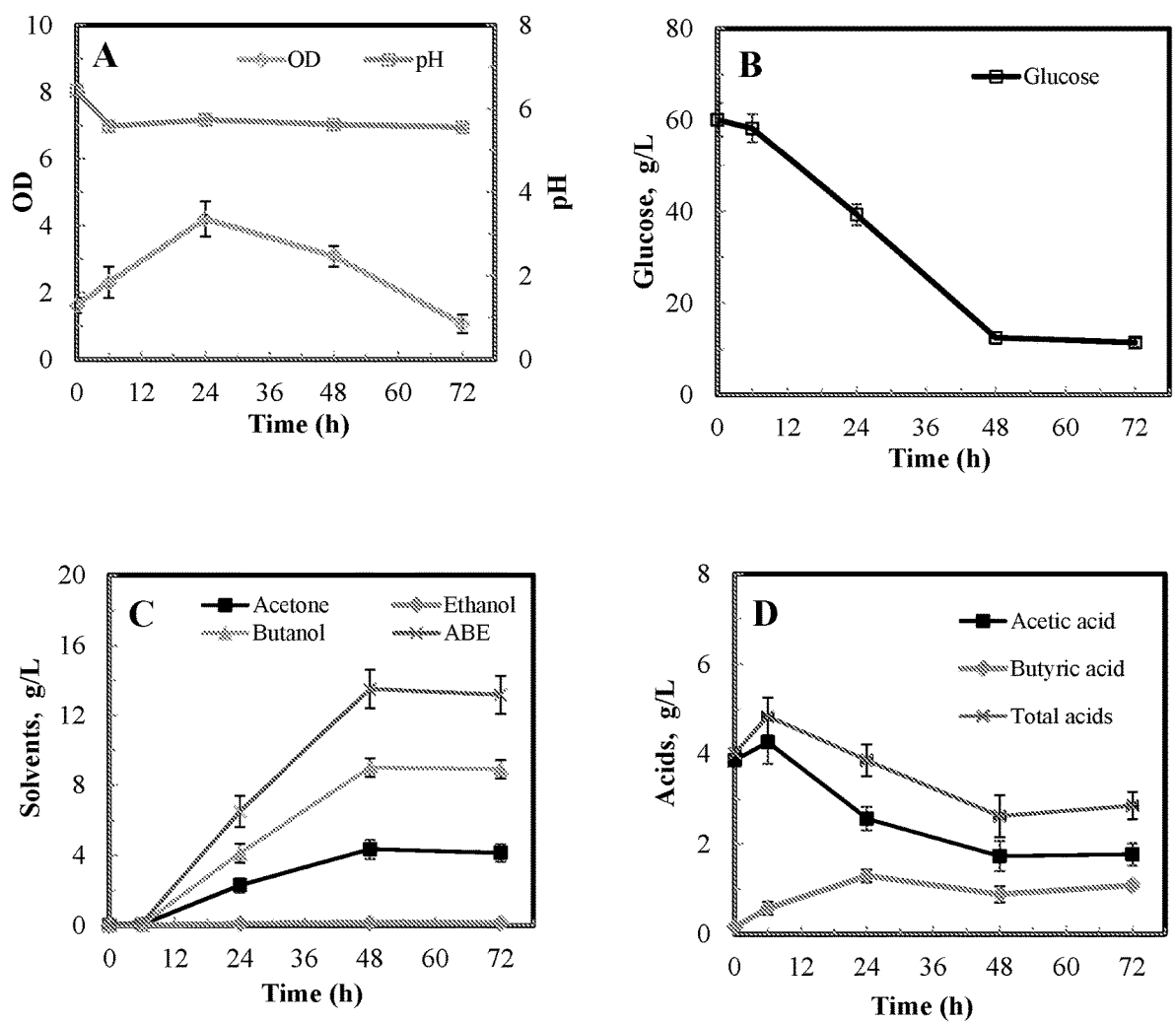
FIG. 5 graphically illustrates (A) Growth and pH, (B) glucose, (C) solvents, and (D) organic acids profiles during ABE fermentation in Fermentor A using *C. acetobutylicum* ATCC 824 with Medium II (redcedar hydrolyzate) (n=3) for an embodiment.

Co-Fermentation of Detoxified Redcedar Hydrolyzate and Generated $CO_2$ and $H_2$ Growth and product profiles of the co-fermentation in Medium II (detoxified redcedar hydrolyzate) in Fermentor A using *C. acetobutylicum* and $CO_2$ and $H_2$ in Fermentor B by *C. ragsdalei* are shown in FIG. 5. Unlike ABE fermentation in Medium I (pure sugar) as shown in FIG. 3, Panel A, the maximum OD in the detoxified hydrolyzate Medium II in Fermentor A was 4.2 units (FIG. 5, Panel A). Lower growth of *C. acetobutylicum* was also reported in an earlier study with redcedar hydrolyzate compared to pure glucose medium (Liu et al., 2015b). However, comparable product profiles were obtained in Fermentor A using Medium I and Medium II (FIGS. 3 and 5). Similar to ABE fermentation in Medium I (pure sugar), pH of Medium II in Fermentor A dropped from 6.4 to 5.6 (FIG. 5, Panel A). At the end of 72 h of fermentation, the residual glucose concentration was 11.4 g/L (FIG. 5, Panel B). The highest butanol and the total ABE production were 8.9 and 13.2 g/L, respectively (FIG. 5, Panel C). The total acid production in Fermentor A was 2.9 g/L.

Figure 6:
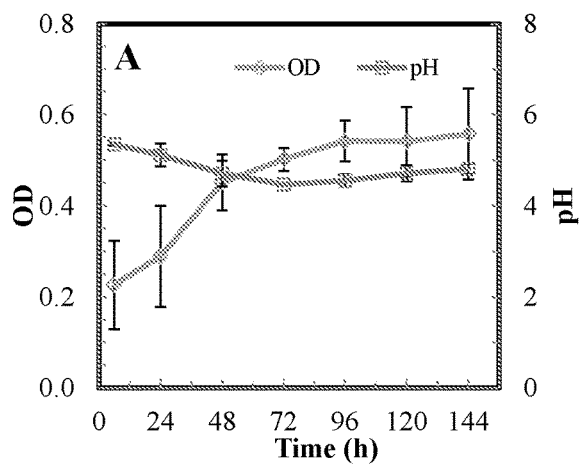
FIG. 6 graphically illustrates (A) Growth and pH, (B) gas consumption/production, (C) ethanol and acetic acid, and (D) absolute headspace pressure profiles during gas fermentation in Fermentor B using *C. ragsdalei* with Medium II (redcedar hydrolyzate) in Fermentor A (n=3) for an embodiment.
Figure 6:
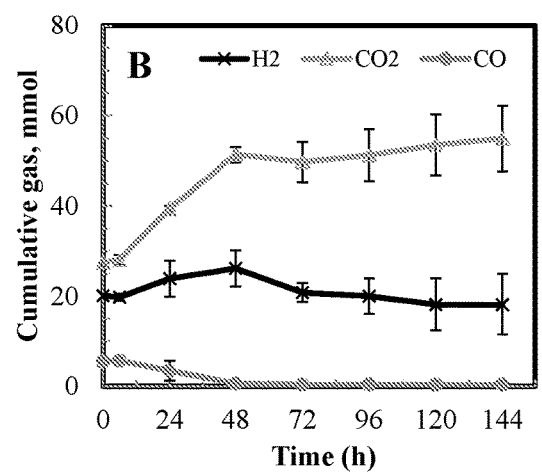
Figure 6:
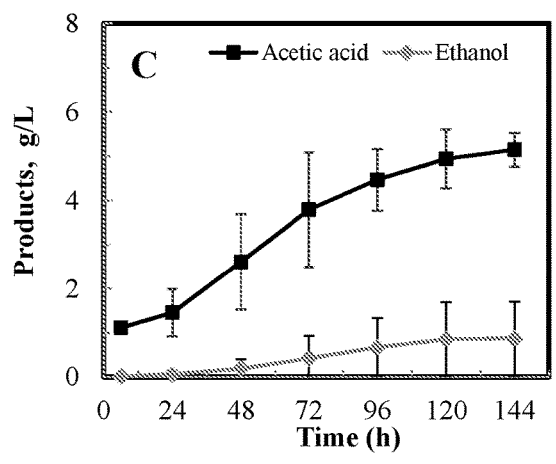
Figure 6:
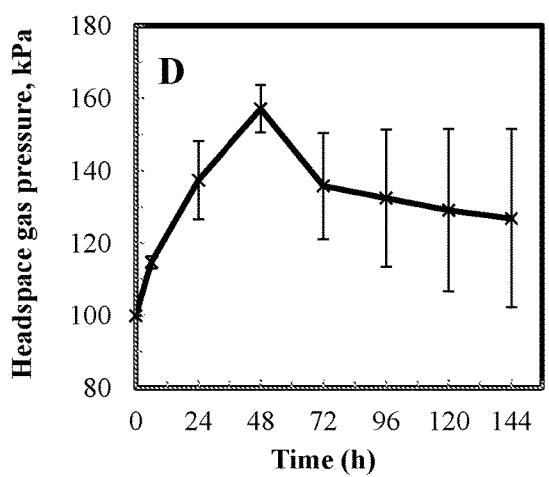

Growth, pH, gas consumption/production, and product profiles of *C. ragsdalei* in Fermentor B are shown in FIG. 6. The maximum OD in Fermentor B was 0.6, and the pH was changed between 5.4 and 4.8. However, ethanol produced from $H_2$ and $CO_2$ generated from Medium II by *C. ragsdalei* in Fermentor B was about 0.9 g/L, which is lower compared to ethanol produced when Medium I was used in Fermentor A (FIG. 4, Panel C; and FIG. 6, Panel C). However, slightly more acid was produced by *C. ragsdalei* in Fermentor B when Medium II was used. *C. ragsdalei* seems to be slightly inhibited when Medium II was used in Fermentor A. The use of co-fermentation has shown 7% and 182% improvements in ABE and total organic acid yields, respectively, due to additional ethanol and acetic acid produced from $H_2$ and $CO_2$.

The use of higher initial *C. ragsdalei* cell concentration in Fermentor B can further enhance gas conversion and production of more ethanol when Medium II is used. FIG. 6, Panel B shows changes in $CO_2$, $H_2$, and CO in headspace of the co-fermentation system. Results showed some $CO_2$ consumption between 48 to 72 h with overall accumulation of $CO_2$. However, similar to the Medium I experiment of Example 1, more than 95% of the initially added CO was utilized during the first 48 h of the fermentation. In addition, less $H_2$ consumption was noticed in Fermentor B, which indicates inhibition of *C. ragsdalei* when Medium II containing redcedar hydrolyzate was used, which warrants further investigation.

The results clearly demonstrated the benefits of co-fermentation of sugars and gases in increasing product yields, while utilizing typically wasted gas streams. This novel process can be used in a multiple reactor system or a single reactor system, with various fermentation modes, and with various other microorganisms to enhance product yields and to reduce emissions of $CO_2$. This novel process can be used to increase revenues of various processes related to food, agriculture, pharmaceutical, environmental, and energy industries.

Thus, in accordance with the present disclosure, there have been provided compositions, as well as methods of producing and using same, which fully satisfy the objectives and advantages set forth hereinabove. Although the present disclosure has been described in conjunction with the specific drawings, experimentation, results, and language set forth hereinabove, it is evident that many alternatives, modifications, and variations will be apparent to those skilled in the art. Accordingly, it is intended to embrace all such alternatives, modifications, and variations that fall within the spirit and broad scope of the present disclosure.

REFERENCES

The following references, to the extent that they provide exemplary procedural or other details supplementary to those set forth herein, are specifically incorporated herein by reference. In addition, the following is not intended to be an Information Disclosure Statement; rather, an Information Disclosure Statement in accordance with the provisions of 37 CFR § 1.97 will be submitted separately.

Ezeji, T. C., Qureshi, N., Blaschek, H. P. 2013. Microbial production of a biofuel (acetone-butanol-ethanol) in a continuous bioreactor: Impact of bleed and simultaneous product removal. Bioprocess and biosystems engineering, 36(1), 109-116.

Fortman, J. L., Chhabra, S., Mukhopadhyay, A., Chou, H., Lee, T. S., Steen, E., Keasling, J. D. 2008. Biofuel alternatives to ethanol: Pumping the microbial well. Trends in Biotechnology, 26(7), 375-381.

Jones, D. T., Woods, D. R. 1986. Acetone-butanol fermentation revisited. Microbiological Reviews, 50(4), 484-524.

Liu, K., Atiyeh, H. K., Tanner, R. S., Wilkins, M. R., Huhnke, R. L. 2012. Fermentative production of ethanol from syngas using novel moderately alkaliphilic strains of *Alkalibaculum bacchi*. Bioresour. Technol., 104, 336-341.

Liu, K., Atiyeh, H. K., Pardo-Planas, O., Ezeji, T. C., Ujor, V., Overton, J. C., Berning, K., Wilkins, M. R., Tanner, R. S. 2015a. Butanol production from hydrothermolysis-pretreated switchgrass: Quantification of inhibitors and detoxification of hydrolyzate. Bioresource technology, 189, 292-301.

Liu, K., Atiyeh, H. K., Pardo-Planas, O., Ramachandriya, K. D., Wilkins, M. R., Ezeji, T. C., Ujor, V., Tanner, R. S. 2015b. Process development for biological production of butanol from eastern redcedar. Bioresource Technology, 176, 88-97.

Mussatto, S. I., Roberto, I. C. 2006. Chemical characterization and liberation of pentose sugars from brewer's spent grain. J. Chem. Technol. Biotechnol., 81(3), 268-274.

Ni, Y., Sun, Z. 2009. Recent progress on industrial fermentative production of acetone-butanol-ethanol by *Clostridium acetobutylicum* in china. Applied Microbiology and Biotechnology, 83(3), 415-423.

Qureshi, N., Saha, B. C., Hector, R. E., Dien, B., Hughes, S., Liu, S., Iten, L., Bowman, M. J., Sarath, G., Cotta, M. A. 2010. Production of butanol (a biofuel) from agricultural residues: Part ii—use of corn stover and switchgrass hydrolysates. Biomass and Bioenergy, 34(4), 566-571.

Ramachandriya, K. D., Wilkins, M. R., Delorme, M. J., Zhu, X., Kundiyana, D. K., Atiyeh, H. K., Huhnke, R. L. 2011.

Reduction of acetone to isopropanol using producer gas fermenting microbes. Biotechnology and bioengineering, 108(10), 2330-2338.

Ramachandriya, K. D., Wilkins, M. R., Hiziroglu, S., Dunford, N. T., Atiyeh, H. K. 2013. Development of an efficient pretreatment process for enzymatic saccharification of eastern redcedar. Bioresour. Technol., 136(0), 131-139.

Simmons, B. A. 2011. Opportunities and challenges in advanced biofuel production: The importance of synthetic biology and combustion science. Biofuels, 2(1), 5-7.

Sluiter, A., Hames, B., Ruiz, R., Scarlata, C., Sluiter, J., Templeton, D. 2008. Determination of ash in biomass. Laboratory analytical procedure (lap). NREL, Golden, Colo.

Wang, B., Ezeji, T., Shi, Z., Feng, H., Blaschek, H. P. 2009. Pretreatment and conversion of distiller's dried grains with solubles for acetone-butanol-ethanol (abe) production. Transactions of the ASABE, 52(3), 885-892.

Wang, L., Chen, H. 2011. Increased fermentability of enzymatically hydrolyzed steam-exploded corn stover for butanol production by removal of fermentation inhibitors. Process biochemistry, 46(2), 604-607.

Yang, B., Wyman, C. E. 2008. Pretreatment: The key to unlocking low cost cellulosic ethanol. Biofuels, Bioproducts and Biorefining, 2(1), 26-40.

Zhu, J. H., Yang, F. 2010. Biological process for butanol production. in: Biomass to renewable energy processes, (Ed.) J. Cheng, CRC Press, pp. 271-336.

What is claimed is:

1. A biocatalytic conversion system that utilizes a co-fermentation process for sugars and gases, the biocatalytic conversion system comprising:
   a first reactor comprising at least one fermentation medium containing at least one first microorganism, wherein the at least one fermentation medium comprises at least one sugar substrate, and wherein the at least one first microorganism comprises a sugar fermenting species, wherein the sugar fermenting species is capable of converting sugars into at least one of acetone, butanol, ethanol, isopropanol, acetic acid, and butyric acid, and wherein the sugar fermenting species is capable of producing a gaseous substrate comprising $CO_2$ and $H_2$ gases during the fermentation process;
   a second reactor comprising at least one medium containing at least one second microorganism, wherein the at least one second microorganism comprises a gas fermenting species, wherein the gas fermenting species is capable of converting $CO_2$ and $H_2$ gases produced during the fermentation of sugars into at least one of an alcohol and an organic acid; and
   a gas line connecting the first reactor to the second reactor for feeding the gaseous substrate produced in the first reactor into the second reactor.

2. The biocatalytic conversion system of claim 1, wherein each of the first and second microorganisms comprises one or more species of microorganisms, and wherein each species is from a genus selected from the group consisting of *Clostridium, Butyribacterium, Eubacterium, Moorella, Acetobacterium, Enterobacter, Bacillus, Anaerobaculum, Alkalibaculum*, and combinations thereof.

3. The biocatalytic conversion system of claim 2, wherein at least one of:
   the first microorganism comprises at least one of *Clostridium acetobutylicum, Bacillus firmus, Anaerobaculum hydrogeniformans*, and *Clostridium beijerinckii*; and
   the second microorganism comprises at least one of *Clostridium ragsdalei, Clostridium autoethanogenum, Clostridium carboxidivorans, Clostridium ljungdahlii*, and *Alkalibaculum bacchi*.

4. The biocatalytic conversion system of claim 3, wherein at least one of:
   the at least one first microorganism comprises *Clostridium acetobutylicum* ATCC 824;
   the at least one second microorganism comprises *Clostridium ragsdalei* P11; and
   the at least one second microorganism comprises *Clostridium carboxidivorans*.

5. The biocatalytic conversion system of claim 1, wherein the at least one sugar substrate present in the at least one fermentation medium in the first reactor is selected from the group consisting of glucose, fructose, sucrose, xylose, galactose, arabinose, mannose, and combinations thereof.

6. The biocatalytic conversion system of claim 1, wherein the at least one sugar substrate of the at least fermentation medium in the first reactor comprises at least one raw material selected from the group consisting of a pure or substantially pure sugar, a starch, cellulose, hemicellulose, other carbohydrates, glucan, xylan, galactan, mannan, cellobiose, lignocellulosic biomass, and combinations thereof.

7. The biocatalytic conversion system of claim 1, wherein the at least one fermentation medium in the first reactor contains a feedstock selected from the group consisting of switchgrass, forage sorghum, grassy materials, redcedar, woody materials, and combinations thereof.

8. The biocatalytic conversion system of claim 7, wherein the feedstock has been pretreated and hydrolyzed prior to placement of the feedstock in the at least one fermentation medium.

9. The biocatalytic conversion system of claim 1, wherein at least one of:
   each of the first and second reactors has a temperature in a range of from about 20° C. to about 45° C., and a pH of the at least one fermentation medium in the first reactor is in a range of from about 4 to about 7.5; and
   external CO and/or $H_2$ gas that is fed into the second reactor.

10. A method of biocatalytic conversion that utilizes a co-fermentation process for sugar and gaseous substrates, the method comprising the steps of:
    contacting at least one fermentation medium with at least one first microorganism in a first reactor, wherein the at least one fermentation medium comprises at least one sugar substrate, and wherein the at least one first microorganism converts the at least one sugar substrate into at least one of acetone, butanol, ethanol, isopropanol, acetic acid, and butyric acid, and wherein a gaseous substrate comprising $CO_2$ and $H_2$ gases is produced during the fermentation process; and
    feeding the gaseous substrate produced in the first reactor into a second reactor, the second reactor comprising at least one medium containing at least one second microorganism, wherein the at least one second microorganism converts $CO_2$ and $H_2$ gases of the gaseous substrate produced in the first reactor and fed into the second reactor into at least one of an alcohol and an organic acid.

11. The method of claim 10, wherein each of the first and second microorganisms comprises one or more species of microorganisms, wherein each species is from a genus selected from the group consisting of *Clostridium, Butyri-* bacterium, Eubacterium, Moorella, Acetobacterium, Enterobacter, Bacillus, Anaerobaculum, Alkalibaculum, and combinations thereof.

12. The method of claim 11, wherein at least one of:
the first microorganism comprises at least one of Clostridium acetobutylicum, Bacillus firmus, Anaerobaculum hydrogeniformans, and Clostridium beijerinckii; and
the second microorganism comprises at least one of Clostridium ragsdalei, Clostridium autoethanogenum, Clostridium carboxidivorans, Clostridium ljungdahlii, and Alkalibaculum bacchi.

13. The method of claim 12, wherein at least one of:
the at least one first microorganism comprises Clostridium acetobutylicum ATCC 824;
the at least one second microorganism comprises Clostridium ragsdalei P11, and wherein ethanol, acetic acid, and isopropanol are produced in the second reactor; and
the at least one second microorganism comprises Clostridium carboxidivorans, and wherein ethanol, butanol, hexanol, butyric acid, acetic acid, and hexanoic acid are produced in the second reactor.

14. The method of claim 10, wherein the at least one sugar substrate present in the at least one fermentation medium in the first reactor is selected from the group consisting of glucose, fructose, sucrose, xylose, galactose, arabinose, mannose, and combinations thereof.

15. The method of claim 10, wherein the at least one sugar substrate of the at least one fermentation medium in the first reactor comprises at least one raw material selected from the group consisting of a pure or substantially pure sugar, a starch, cellulose, hemicellulose, other carbohydrates, glucan, xylan, galactan, mannan, cellobiose, lignocellulosic biomass, and combinations thereof.

16. The method of claim 10, wherein the at least one fermentation medium in the first reactor contains a feedstock selected from the group consisting of switchgrass, forage sorghum, grassy materials, redcedar, woody materials, and combinations thereof.

17. The method of claim 16, further comprising the step of pretreating and hydrolyzing the feedstock prior to contact with the at least one first microorganism.

18. The method of claim 10, further defined as producing at least one alcohol, at least one ketone, and at least one organic acid.

19. The method of claim 10, wherein at least one of:
each of the first and second reactors is maintained at a temperature in a range of from about 20° C. to about 45° C., and a pH of the at least one fermentation medium in the first reactor is maintained in a range of from about 4 to about 7.5; and
the method further comprises the step of feeding additional CO and/or $H_2$ gas into the second reactor.

20. The biocatalytic conversion system of claim 1, wherein the gas line connects a headspace of the first reactor to the headspace of the second reactor.

21. The method of claim 10, wherein the step of feeding the gaseous substrate produced in the first reactor into the second reactor is further defined as feeding the gaseous substrate from a headspace of the first reactor into a headspace of the second reactor.

22. The method of claim 10, wherein the step of feeding the gaseous substrate produced in the first reactor into the second reactor is further defined as bubbling the gaseous substrate into the at least one medium of the second reactor.

* * * * *

UNITED STATES PATENT AND TRADEMARK OFFICE
CERTIFICATE OF CORRECTION

PATENT NO. : 11,180,779 B2
APPLICATION NO. : 16/604242
DATED : November 23, 2021
INVENTOR(S) : Hasan K. Atiyeh Page 1 of 1

It is certified that error appears in the above-identified patent and that said Letters Patent is hereby corrected as shown below:

In the Specification

Column 13, Line 19: Delete "Hz," and replace with -- $H_2$ --

Column 13, Line 28: Delete "Hz," and replace with -- $H_2$ --

Column 13, Line 45: Delete "Hz," and replace with -- $H_2$ --

Column 17, Line 53: Delete "Hz," and replace with -- $H_2$ --

Signed and Sealed this
Fourth Day of January, 2022

Drew Hirshfeld
*Performing the Functions and Duties of the*
*Under Secretary of Commerce for Intellectual Property and*
*Director of the United States Patent and Trademark Office*